United States Patent [19]

Man

[11] Patent Number: Plant 7,163

[45] Date of Patent: Feb. 20, 1990

[54] BEGONIA PLANT NAMED 'LARESSA'

[75] Inventor: Jan Man, Lisse, Netherlands

[73] Assignee: Oglevee, Ltd., Connellsville, Pa.

[21] Appl. No.: 254,277

[22] Filed: Oct. 6, 1988

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

A new Begonia variety is characterized by its vigorous growth and resultant strong plant. The color of the bloom is bright and clear and pleasing to the eye. The new cultivar has a high tolerance to botrytis and powdery mildew.

1 Drawing Sheet

BACKGROUND OF THE NEW PLANT

The present invention comprises a new and distinct cultivar of *Begonia*×*hiemalis* known by the varietal name of Laressa. The new cultivar is a selection of a cross between the seed parent Lara and the pollen parent Ilona. The new cultivar has a plant form and foliage similar to Lara. The flower color, however, is slightly darker than Lara and the flower form is double whereas the flower form of Lara is single.

The new cultivar was discovered in April of 1981 at Limaplant b.v. in Lisse, Holland; was first asexually reproduced by cuttings at Limaplant b.v. in Lisse, Holland; and has been repeatedly asexually reproduced by cuttings for Oglevee Ltd. in Connellsville, Pa. It has been found to retain its distinctive characteristics through successive propagations.

The new cultivar is generally characterized by its vigorous growth and resultant strong plant. The color of the bloom is bright and clear and pleasing to the eye. The new cultivar has a high tolerance to botrytis and powdery mildew.

The new cultivar, when grown in a greenhouse in Connellsville, Pa., has a response time of nine to ten weeks from a well-rooted cutting to a flowering finished plant in a six-inch pot (no pinch).

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out for Oglevee Ltd. in Connellsville, Pa. The plant history was taken on ten week plants blossomed under natural light in a greenhouse and grown under temperature conditions of 62° F. at night and 68° F. during the day. The plants were potted in a peat-lite mix and fertilized with a 100 ppm mixture of 15N-OP-15K. Color readings were taken indoors under 200 footcandles of cool white fluorescent tubes. Color references are to The R.H.S. Colour Chart of The Royal Horticultural Society of London, unless noted differently.

Botanical classification: *Begonia*×*hiemalis.*

Flower:

*Fully expanded.*—4.5 cm. in diameter; side view — flattened oval.

*Borne.*—Compound dichasium (cyme).

*Stems.*—Strong, upright stems; average stem width 4 cm., color yellow-green group 152C.

*Form.*—Double; each flower has 2 sepals, 7 petals, 7 petaloids (each group may vary ±1 structure).

*Permanence.*—Very long lasting bloom, average life span 2–3 weeks.

Color:

*Tonality from a distance.*—Base hue of dark pink with overtones of scarlet, yellow and orange.

*Front of petals.*—Red group 41C; as you move toward the bottom of a petal, slight tones of orange and yellow appear.

*Reverse of petals.*—Outer edge area: red group 48B; inner side area; slight orange tone.

*Base of petals.*—Yellow group 11B.

*Throat.*—None.

*Other comments.*—Flower color tends to be darker at outer edges and moves to lighter tones and hues of orange and yellow toward the center. Outer edges red group 47C and overall tight bud color red group 44C.

Petals:

*Texture.*—Crepe paper like (gentle crinkles).

*Appearance.*—Oval with color gradient. Outer edge: dark pink→light pink with orange overtone→yellow attachment.

*Arrangement.*—Semi- to fully double.

*Persistence.*—Very good flowering response, produces high number of buds.

*Fragrance.*—None.

Reproductive organs: All reproductive organs have modified into petaloids. Anthers, filament, pollen and style could not be observed.

Plant:

*Form.*—Short, compact, internodes 2–3 cm apart, good basal branching; strong stems give good self-support.

*Growth.*—Very vigorous; plant growth can be modified by changing environmental conditions in which plant was grown (higher temperatures will give faster and lusher growth).

*Height from soil line.*—18–20 cm in 11 weeks (no pinch, no cycocel).

*Spread.*—26–28 cm in 11 weeks (no pinch, no cycocel).

Foliage:

*Size.*—Depends on how plant was grown and position of leaf on plant; average length of 12 cm and average width of 6 cm.

*Quantity.*—Very abundant.

*Shape.*—Acute tip with irregularly lobed attachment; edge is slightly doubly serrate.

*Top side.*—Green group 137A; shiny and smooth.

*Underside.*—Green group 138A; to 138B.

*Ribs and veins.*—Smooth on top, raised on lower side, lower side of veins only area where tricomes (hairs) appear.

*Rib and vein color.*—Top side: yellow-green group 144B; bottom side: yellow-green group 146D.

*Margin.*—None.

*Stipules.*—None.

*Texture.*—Top: smooth, shiny and leathery; bottom: matt finish with raised veins.

I claim:

1. A new and distinct variety of Begonia characterized by its vigorous growth, resultant strong plant, color of the bloom bright and clear and pleasing to the eye, and high tolerance to botrytis and powdery mildew as herein shown and described.

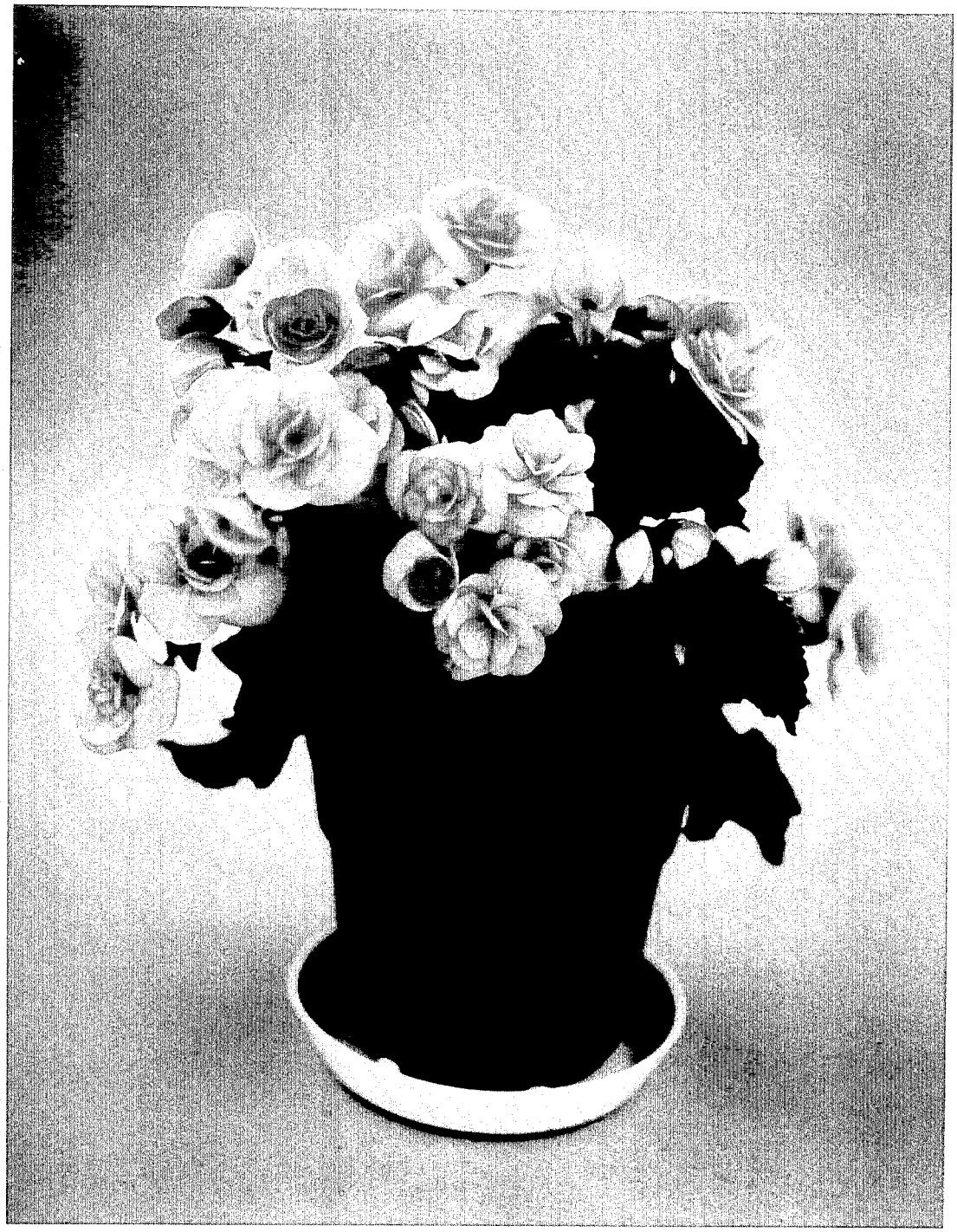

* * * * *